United States Patent [19]

Polymeropoulos et al.

[11] Patent Number: 5,378,602

[45] Date of Patent: * Jan. 3, 1995

[54] HIGHLY INFORMATIVE MICROSATELLITE REPEAT POLYMORPHIC DNA MARKERS TWENTY-[SEVEN]SIX

[75] Inventors: Michael H. Polymeropoulos, Bethesda; Carl R. Merril, Rockville, both of Md.

[73] Assignee: The Government of the United States of America as represented by the Secretary of the Department of Health and Human Services, Washington, D.C.

[*] Notice: The portion of the term of this patent subsequent to Nov. 29, 2011 has been disclaimed.

[21] Appl. No.: 799,828

[22] Filed: Nov. 27, 1991

Related U.S. Application Data

[63] Continuation-in-part of Ser. No. 707,501, May 29, 1991, abandoned.

[51] Int. Cl.[6] ............... C12Q 1/68; C12P 19/34; C07H 21/04
[52] U.S. Cl. ..................... 435/6; 435/91.2; 536/24.31; 536/24.33
[58] Field of Search ............ 536/24.33, 24.31; 435/91, 6, 91.2

[56] References Cited

U.S. PATENT DOCUMENTS

| | | | |
|---|---|---|---|
| 4,683,195 | 7/1987 | Mullis et al. | 435/91.2 |
| 4,683,202 | 7/1987 | Mullis | 435/91.2 |
| 4,800,159 | 6/1989 | Mullis et al. | 435/91 |
| 4,879,214 | 11/1989 | Kornher et al. | 435/91.2 |
| 5,001,050 | 3/1991 | Blanco et al. | 435/5 |

OTHER PUBLICATIONS

Zuliani et al. (1990) Nucl. Acids. Res. 18:4299, "Tetranucleotide repeat polymorphism in the apolipoprotein C–III gene".
Zuliani et al. (1990) Nucl. Acids. Res. 18 (16): 4958, "Tetranucleotide repeat polymorphism in the LPL gene".
Ploos et al. (1990) Nucl. Acids. Res. 18 (16): 4957, "Tetranucleotide repeat polymorphism in the VWF gene".
Gasparini et al. 91991) Human Genetics 86: 625, "A tetranucleotide repeat polymorphism in the cystic fibrosis gene".
Ali et al. (1986) Human Genetics 74:239–243, "DNA finger printing by oligonucleotide probes Specific for simple repeats".

(List continued on next page.)

*Primary Examiner*—Mindy B. Fleisher

[57] ABSTRACT

The invention relates to polymorphic markers (two tetranucleotide, one dinucleotide repeat polymorphisms and 27 markers characterized by primer pairs 1A–27A) that are useful for human individualization. Applications are in forensic medicine and for paternity and prenatal screening as well as genetic mapping. These markers are characterized by sets of oligonucleotide primers according to the invention useful in PCR amplification and DNA segment resolution.

The invention further relates to an assay for measuring the subtle differences in genetic material regarding an added or omitted set of dinucleotide or tetranucleotide repeat polymorphisms which comprises obtaining an amount of nucleotide segments effective for testing, amplifying the segments by the PCR procedure using at least one primer nucleotide sequence according to the present invention, resolving the amplified segments using gel electrophoresis, and comparing the resolved segments by autoradiography to observe the differences in migration patterns due to structural differences. The assay according to the invention is easy to perform and results can be obtained within 24 hours. It is not uncommon results to be available within 3–4 hours. Accordingly, the invention also relates to an improved PCR procedure and a PCR assay kit which comprise nucleotides according to the invention.

4 Claims, 8 Drawing Sheets

OTHER PUBLICATIONS

Dean et al. (1990, Jan. 25) Nucl. Acids Res. 18(2): 345–350,* "Approaches to localizing disease genes as applied to cystic fibrosis".

Dariavach et al., "Human Ig Superfamily CTLA–4 Gene: Chromosomal Localization and Identity of Protein Sequence Between Murine and Human CTLA–4 Cytoplasmic Domains", European Journal of Immunology, vol. 18, pp. 1901–1905 (1988).

Weber et al. Abundant Class of Human DNA Polymorphisms Which can be Typed Using the Polymerase Chain Reaction, Am. Hum. Genet., vol. 44, pp. 388–396 (1989).

Moos et al., "Structure of Two Human Beta-Actin-related Processed Genes One of Which is Located Next to a Simple Repetitive Sequence", Embo Journal, vol. 2, No. 5, pp. 757–761, (1983).

Chen et al., "The Human Growth Hormone Locus: Nucleotide Sequence, Biology, and Evolution", Genomic, vol. 2, pp. 479–497 (1989).

Weber et al. Dinucleotide Repeat Polymorphism at the DIOS89 Locus, Nucleic Acids Research, vol. 18, No. 15, p. 4637.

Weber et al., Dinucleotide Repeat Polymorphism at the D12S43 Locus, Nucleic Acids Research, vol. 18, No. 15, p. 4637.

Tautz et al., Nucleic Acids Research, vol. 12, No. 10, 1984, pp. 4127–4138.

Nakamura et al. Variable Number of Tandem Repeat (VNTR) Markers for Human Gene Mapping, Science, vol. 235, 2987, pp. 1616–1622.

Jeffreys et al., Spontaneous Mutation Rates to New Length Alleles at Tandem-Repetitive Hypervariable Loci in Human DNA, Nature, vol. 332, 1988, pp. 278–281.

Overhauser et al. Nucleic acids Research, vol. 15, No. 11, 1987, pp. 4617–4627.

Jeffreys et al., Hypervariable "minisatellite" regions in Human DNA, Nature, vol. 314, 1985, pp. 67–73.

Weber et al., Abundant Class of Human DNA Polymorphisms Which can be Typed Using the Polymerase Chain Reaction, Am. Hum. Genet., vol. 44, pp. 388–396 (1989).

Engelke et al. Direct sequencing of enzymatically amplified human genomic DNA, Proc. Natl. Acad. U.S.A., vol. 85, pp. 544–548 (1988).

Wong et al., Characterization of $\beta$-thalassaemia mutations using direct genomic sequencing; of amplified single copy DNA, Nature, vol. 330, pp. 384–386 (1987).

Botstein et al., Construction of a Genetic Linkage Map in Man Using Restriction Fragment Length Polymorphisms Am. J. Hum. Genet., vol. 32, pp. 314–331 (1980).

White et al., Chromosome Mapping with DNA Markers, Scientific American, vol. 258, pp. 40–48 (1988).

Wallace et al. The use of synthetic oligonucleotides as hybridization probes. II Hybridization of oligonucleotides of mixed sequence to rabbit $\beta$-globin DNA, Nucl. Acid Research, vol. 9, pp. 879–984 (1981).

Litt et al., A Hypervariable Microsatellite Revealed by In Vitro Amplification of a Dinucleotide Repeat within the Cardiac Muscle Actin Gene, Human Genet., vol. 44, pp. 397–401 (1989).

FIGURE 1

AATCTGGGCG ACAAGAGTGA                    20

FIGURE 2

ACATCTCCCC TACCGCTATA                    20

FIGURE 3

TCCAGCCTCG GAGACAGAAT                    20

FIGURE 4

AGTCCTTTCT CCAGAGCAGG T                  21

FIGURE 5

GCCAGTGATG CTAAAGGTTG                    20

FIGURE 6

AACATACGTG GCTCTATGCA                    20

FIGURE 7

```
AATCTGGGCG ACAAGAGTGA AACTCCGTCA AAAGAAAGAA AGAAAGAGAC    50
AAAGAGAGTT AGAAAGAAAG AAAGAGAGAG AGAGAGAAAG GAAGGAAGGA   100
AGAAAAAGAA AGAAAAAGAA AGAAAGAGAA AGAAAGAAAG AGAAAGAAAG   150
AAAGAAAGAA AGAAAGAAAG AAAGAAAGAA AGAAAGAAAA AGAAAGAAAG   200
AAAGAAAGAA AGAAAGAAAG AAAGAAAGAA AGAAAGAAAG AAAGAAAGGA   250
AGGAAAGAAA GAGCAAGTTA CTATAGCGGT AGGGGAGATG T            291
```

FIGURE 8

```
GCCAGTGATG CTAAAGGTTG TATTGCATAT ATACATATAT ATATATATAT    50
ATATATATAT ATATATATAT ATATATATAT ATATATATAT TTTAATTTGA   100
TAGTATTGTG CATAGAGCCA CGTATGTT                           128
```

FIGURE 9

```
TCCAGCCTCG GAGACAGAAT GAGACTCCAT CAAAAACAAG AAAGAAAGAA    50
AGACAAAGAG AGAAAGAAAG AAAGAAAGAA AGAAAGAAAG AGAGAGAGAG   100
AGAGAGAGAG AGAAAGAAAG AAAGAAAGAA AGAAAGAAAG AAAGAAAGAA   150
AGAAAGAAAG AAAGAAAGAA GGAAAGAAAG AAAGGAAACT AAAATAACTA   200
AATAACTGAG TAGCACCACA CCACCTGCTC TGGAGAAAGG ACT          243
```

FIGURE 10

```
TTTCTGGGTG TGTCTGAAT                                      19
```

FIGURE 11

```
ACACAGTTGC TCTAAAGGGT                                     20
```

FIGURE 12
CTAGGTTGTA AGCTCCATGA                 20

FIGURE 13
TTGAGCACTT ACTCTGTGCC                 20

FIGURE 14
AACTCAGAAC AGTGCCTGAC                 20

FIGURE 15
ATTTCCCTCA AGGCTCCAGG T               21

FIGURE 16
CTGATCTTGC TCACCTTCGA                 20

FIGURE 17
GCGTTTGCTG AAATGAAGGA                 20

FIGURE 18
GCAGGTACTT AGTTAGCTAC                 20

FIGURE 19
TTACAGTGAG CCAAGGTCGT                 20

FIGURE 20
TTTGTCTGGA TAGACTGGAG                 20

FIGURE 21
CCATCTTCCT GTGGCTGTA                      19

FIGURE 22
CTAATGCAGA GATTTAGGGC                     20

FIGURE 23
GTGGTGTAAA GACTGCATAG                     20

FIGURE 24
ATGTGACTGA TGTGGGTCAG                     20

FIGURE 25
CATCTGCACT CATGCTCCAT                     20

FIGURE 26
TCCCAGATCG CTCTACATGA                     20

FIGURE 27
CACAGCTTCA GAAGTCACAG                     19

FIGURE 28
GAGCAATGTT GCTTAGGATG                     20

FIGURE 29
TGGAAGTGTC ACTGGCATGT                     20

FIGURE 30

TGTGTCCAGC CTTAGTGTGC A      21

FIGURE 31

TCATCACTTC CAGAATGTGC      20

FIGURE 32

ACTGCCTCAT CCAGTTTCAG      20

FIGURE 33

GAGCAGGCAC TTGTTAGATG      20

FIGURE 34

CCTCTTGGCT CTAACAGCAA      20

FIGURE 35

AGCAAGACCC TGTCTCAAGA      20

FIGURE 36

CAAGGCCCAT CTTCAGTAGA      20

FIGURE 37

CCTTCTCACT CCTTTACTAG      20

FIGURE 38

GAAGACTGAG GAGGTCAGAA      20

FIGURE 39

CTACTGTTCA GAGTCAAAGC 20

FIGURE 40

TGCCCCACAT TAGGATGCAT 20

FIGURE 41

AGGGACACGA ATCAGATCAG 20

FIGURE 42

GTGGTACCTC ATTGTGGCTA 20

FIGURE 43

AGGCATCCTT GTGCTGACAT 20

FIGURE 44

TTTGGCCGAC AGTGGTGTAA 20

FIGURE 45

AGGACCAAAC CATGTCTGTC 20

FIGURE 46

CTGCATCTGA GCATATGGGA 20

FIGURE 47

CATTCAGACT ATGCAGGCTT 20

FIGURE 48
CTGGGACTAC TGGCACATG                    19

FIGURE 49
GGCAACGTGG TGAAACCTT                    19

FIGURE 50
GGAAGATGGA GTGGCTGTTA                   20

FIGURE 51
CTCCAGCCTG GCGAAAGAAT                   20

FIGURE 52
GTAAGACTTT TGGAGCCATT                   20

FIGURE 53
TTCAGGGAGA ATGAGATGGG                   20

FIGURE 54
GACAGAGTGA GACTCCATCT                   20

FIGURE 55
GATCCTATCT TCTCAGGAGG                   20

FIGURE 56
GAGGTTGCAC TCCAGCCTTT                   20

FIGURE 57

ATGCCATGCA GATTAGAAA                        19

FIGURE 58

GGAAAGAAAC AGTGAAAGA                        19

FIGURE 59

ATCCATCGAC CTCTGGGTTA                       20

FIGURE 60

GACCCCACAG CCTATTCAGA                       20

FIGURE 61

TTGACTGCTG AACGGCTGCA                       20

FIGURE 62

CAGCTGCCCT AGTCAGCAC                        19

FIGURE 63

GCTTCCGAGT GCAGGTCACA                       20

HIGHLY INFORMATIVE MICROSATELLITE REPEAT POLYMORPHIC DNA MARKERS TWENTY-[SEVEN]SIX

This application is a continuation-in-part of co-pending application 07/707,501 filed May 29, 1991, now abandoned.

TECHNICAL FIELD

This application relates to genetic testing with polymorphic DNA markers having repeat sequences to provide a rapid and convenient high resolution process for distinguishing target nucleic acid segments on the basis of nucleotide differences according to human individualization wherein the nucleic acid segments differ in size.

BACKGROUND ART

The science of genetics has taken a keen interest in the identification of human individualization and genetic relationships between individuals. Each individual has hereditary material (DNA, "nucleotides") which is unique to that individual and hereditary material which is related to that of others. Procedures have been developed which are based on identification and characterization of changes in DNAs, which are changes in DNA (DNA polymorphisms) due to nucleotide substitution, insertion, or deletion within the chains of DNAs.

In the field of forensic medicine, for example, there is a keen interest in such polymorphisms for identification purposes. Forensic geneticist have developed many techniques to compare homologous segments of DNA to determine if the segments are identical or if they differ in one or more nucleotides. Practical applications of these techniques relate to fields other than forensic medicine, for example, genetic disease diagnosis and human genome mapping.

At the present time in this art, the most accurate and informative way to compare DNA segments requires a method which provides the complete nucleotide sequence for each DNA segment. Particular techniques have been developed for determining actual sequences in order to study mutation in human genes. See, for example, Proc. Natl. Acad. Sci. U.S.A. 85, 544–548 (1988) and Nature 330, 384–386 (1987). However, because of the extensive amounts of time and high costs to determine, interpret, and compare sequence information, presently it is not practical to use extensive sequencing for compare more than just a few DNA segments.

In genetic mapping, the most frequently used screening for DNA polymorphisms arising from mutations consist of digesting the DNA strand with restriction endonucleases and analyzing the resulting fragments by means of Southern blots. See Am. J. Hum. Genet. 32, 314–331 (1980) or Sci. Am. 258, 40–48 (1988). Since mutations often occur randomly they may affect the recognition sequence of the endonuclease and preclude the enzymatic cleavage at that cite. Restriction fragment length polymorphism mappings (RFLPS) are based on changes at the restriction site. They are accurate but not very informative (PIC [0.3). The major problem with RFLPs is the inability of a test to detect changes that do not affect cleavage with a restriction endonuclease. As in many of the test methods in the DNA art, the methods used to detect RFLPs are very labor intensive and expensive, especially the techniques which includes Southern blot analysis.

Another technique for detecting specific mutations in particular DNA segment involves hybridizing DNA segments which are being analyzed (target DNA) with a complimentary, labeled oligonucleotide probe. See Nucl. Acids Res. 9, 879–894 (1981). Since DNA duplexes containing even a single base pair mismatch exhibit high thermal instability, the differential melting temperature can be used to distinguish target DNAs that are perfectly complimentary to the probe from target DNAs that only differ by a single nucleotide. This method has been adapted to detect the presence or absence of a specific restriction site, U.S. Pat. No. 4683,194. The method involves using an end-labeled oligonucleotide probe spanning a restriction site which is hybridized to a target DNA. The hybridized duplex of DNA is then incubated with the restriction enzyme appropriate for that site. Reformed restriction sites will be cleaved by digestion in the pair of duplexes between the probe and target by using the restriction endonuclease. The specific restriction site is present in the target DNA if shortened probe molecules are detected.

Another process for studying differences in DNA structure is the primer extension process which consists of hybridizing a labeled oligonucleotide primer to a template RNA or DNA and then using a DNA polymerase and deoxynucleoside triphosphates to extend the primer to the 5' end of the template. Resolution of the labeled primer extension product is then done by fractionating on the basis of size, e.g., by electrophoresis via a denaturing polyacrylamide gel. This process is often used to compare homologous DNA segments and to detect differences due to nucleotide insertion or deletion. Differences due to nucleotide substitution are not detected since size is the sole criterion used to characterize the primer extension product.

Another process exploits the fact that the incorporation of some nucleotide analogs into DNA causes an incremental shift of mobility when the DNA is subjected to a size fractionation process, such as electrophoresis. Nucleotide analogs can be used to identify changes since they can cause an electrophoretic mobility shift. See, U.S. Pat. No. 4,879,214.

Unfortunately, the above techniques used for identification of polymorphisms are either not very informative or take a long period of time to perform. For example, techniques which identify changes in individual nucleotides on a particular DNA strand often take at least three to four days to perform. Accordingly, such tests are very labor intensive and expensive to perform.

Further, subtle genetic differences among related individuals regarding nucleotides which are substituted in the DNA chains are difficult to detect. VNTR's or Jeffrey's probes (which the FBI is using to test and identify DNA chains) are very informative but labor intensive, in distinction to microsatellites as our which are equally informative PCR based polymormismic.

The use of certain nucleotide repeat polymorphisms for identifying or comparing DNA segments have been described by Weber & May 89 Am Hum Genet 44:388, Litt & Luthy '89 Am) Hum Genet 44:397). However the particular polymorphism genetic segments and primers used to identify the polymorphisms (for identification and comparison purposes) of the present invention have not been previously known or suspected.

Accordingly, there a need in this art for a rapid, simple, inexpensive and accurate technique having a very high resolution value to determine relationships between individuals and differences in degree of relationships. Also, there is a need in the art for a very accurate genetic relationship test procedure which uses very small amounts of an original DNA sample, yet produces very accurate results. This is particularly true in the forensic medicine area and criminology, since often times very small samples of DNA are available for testing.

DISCLOSURE OF THE INVENTION

An object of the present invention is to provide a fast and accurate test for measuring the subtle differences in individuals by way of genetic testing.

Another object of the invention relates to polymorphic markers that can be used for human individualization.

A further object of the invention is to provide a fast and accurate technique for measuring the subtle differences in individuals by way of genetic testing that can be applied in multiple areas, e.g., forensic screening, paternity and prenatal screening and genetic mapping.

A still further object is to provide an improved method for conducting a PCR procedure using an effective amount of a nucleotide according to the present invention and to provide an PCR assay kit comprising an effective amount of a nucleotide according to the present invention and ancillary PCR reagents.

BRIEF DESCRIPTION OF THE DRAWINGS

FIG. 1 relates to a nucleotide sequence according to SEQ ID NO:1.

FIG. 2 relates to a nucleotide sequence according to SEQ ID NO:2.

FIG. 3 relates to a nucleotide sequence according to SEQ ID NO:3.

FIG. 4 relates to a nucleotide sequence according to SEQ ID NO:4.

FIG. 5 relates to a nucleotide sequence according to SEQ ID NO:5.

FIG. 6 relates to a nucleotide sequence according to SEQ ID NO:6.

FIG. 7 relates to a nucleotide sequence according to SEQ ID NO:7.

FIG. 8 relates to a nucleotide sequence according to SEQ ID NO:8.

FIG. 9 relates to a nucleotide sequence according to SEQ ID NO:9.

FIG. 10 relates to a nucleotide sequence according to SEQ ID NO:10.

FIG. 11 relates to a nucleotide sequence according to SEQ ID NO:11.

FIG. 12 relates to a nucleotide sequence according to SEQ ID NO:12.

FIG. 13 relates to a nucleotide sequence according to SEQ ID NO:13.

FIG. 14 relates to a nucleotide sequence according to SEQ ID NO:14.

FIG. 15 relates to a nucleotide sequence according to SEQ ID NO:15.

FIG. 16 relates to a nucleotide sequence according to SEQ ID NO:16.

FIG. 17 relates to a nucleotide sequence according to SEQ ID NO:17.

FIG. 18 relates to a nucleotide sequence according to SEQ ID NO:18.

FIG. 19 relates to a nucleotide sequence according to SEQ ID NO:19.

FIG. 20 relates to a nucleotide sequence according to SEQ ID NO:20.

FIG. 21 relates to a nucleotide sequence according to SEQ ID NO:21.

FIG. 22 relates to a nucleotide sequence according to SEQ ID NO:22.

FIG. 23 relates to a nucleotide sequence according to SEQ ID NO:23.

FIG. 24 relates to a nucleotide sequence according to SEQ ID NO:24.

FIG. 25 relates to a nucleotide sequence according to SEQ ID NO:25.

FIG. 26 relates to a nucleotide sequence according to SEQ ID NO:26.

FIG. 27 relates to a nucleotide sequence according to SEQ ID NO:27.

FIG. 28 relates to a nucleotide sequence according to SEQ ID NO:28.

FIG. 29 relates to a nucleotide sequence according to SEQ ID NO:29.

FIG. 30 relates to a nucleotide sequence according to SEQ ID NO:30.

FIG. 31 relates to a nucleotide sequence according to SEQ ID NO:31.

FIG. 32 relates to a nucleotide sequence according to SEQ ID NO:32.

FIG. 33 relates to a nucleotide sequence according to SEQ ID NO:33.

FIG. 34 relates to a nucleotide sequence according to SEQ ID NO:34.

FIG. 35 relates to a nucleotide sequence according to SEQ ID NO35.

FIG. 36 relates to a nucleotide sequence according to SEQ ID NO:36.

FIG. 37 relates to a nucleotide sequence according to SEQ ID NO:37.

FIG. 38 relates to a nucleotide sequence according to SEQ ID NO:38.

FIG. 39 relates to a nucleotide sequence according to SEQ ID NO:39.

FIG. 40 relates to a nucleotide sequence according to SEQ ID NO:40.

FIG. 41 relates to a nucleotide sequence according to SEQ ID NO:41.

FIG. 42 relates to a nucleotide sequence according to SEQ ID NO:42.

FIG. 43 relates to a nucleotide sequence according to SEQ ID NO:43.

FIG. 44 relates to a nucleotide sequence according to SEQ ID NO:44.

FIG. 45 relates to a nucleotide sequence according to SEQ ID NO:45.

FIG. 46 relates to a nucleotide sequence according to SEQ ID NO:46.

FIG. 47 relates to a nucleotide sequence according to SEQ ID NO:47.

FIG. 48 relates to a nucleotide sequence according to SEQ ID NO:48.

FIG. 49 relates to a nucleotide sequence according to SEQ ID NO:49.

FIG. 50 relates to a nucleotide sequence according to SEQ ID NO:50.

FIG. 51 relates to a nucleotide sequence according to SEQ ID NO:51.

FIG. 52 relates to a nucleotide sequence according to SEQ ID NO:52.

FIG. 53 relates to a nucleotide sequence according to SEQ ID NO:53.

FIG. 54 relates to a nucleotide sequence according to SEQ ID NO:54.

FIG. 55 relates to a nucleotide sequence according to SEQ ID NO:55.

FIG. 56 relates to a nucleotide sequence according to SEQ ID NO:56.

FIG. 57 relates to a nucleotide sequence according to SEQ ID NO:57.

FIG. 58 relates to a nucleotide sequence according to SEQ ID NO:58.

FIG. 59 relates to a nucleotide sequence according to SEQ ID NO:59.

FIG. 60 relates to a nucleotide sequence according to SEQ ID NO:60.

FIG. 61 relates to a nucleotide sequence according to SEQ ID NO:61.

FIG. 62 relates to a nucleotide sequence according to SEQ ID NO:62.

FIG. 63 relates to a nucleotide sequence according to SEQ ID NO:63.

BEST MODE FOR CARRYING OUT THE INVENTION

The present invention provides a fast and accurate test for measuring subtle genetic differences in individuals by way of genetic testing. The invention further relates to polymorphic markers (two tetranucleotide and one dinucleotide repeat polymorphisms) that can be used for human individualization. The invention further relates to 27 other polymorphic markers useful for human individualization. Applications for the technique and markers according to the invention are for example, in forensic screening, in paternity and prenatal screening as well as in genetic mapping. The invention relates to polymorphic markers (two tetranucleotide, one dinucleotide repeat polymorphisms and 27 other unique polymorphic markers) that are useful for human individualization of forensic screen, and for paternity and prenatal screening as well as genetic mapping. The markers according to the present invention have high polymorphism information content (PIC) values. The first three markers are characterized by sets of oligonucleotide primers as follows:

1. Set 1, PIC 0.92
   a. A nucleotide sequence according to SEQ ID NO:1
   b. A nucleotide sequence according to SEQ ID NO:2
2. Set 2, PIC 0.91
   a. A nucleotide sequence according to SEQ ID NO:3
   b. A nucleotide sequence according to SEQ ID NO:4
3. Set 3, PIC 0.92
   a. A nucleotide sequence according to SEQ ID NO:5
   b. A nucleotide sequence according to SEQ ID NO:6.

These polymorphic markers (two tetranucleotide and one dinucleotide repeat polymorphisms which are also accompanied by beginning and ending nucleotide sequences) that can be used for human individualization are further characterized by the following marker sequences.

1. A nucleotide sequence having a repeat polymorphism according to SEQ ID NO:7.
2. A nucleotide sequence having a repeat polymorphism according to SEQ ID NO:8.
3. A nucleotide sequence having a repeat polymorphism according to SEQ ID NO:9.

Since a polymorphic marker and an index locus occur as a "pair", attaching a primer oligonucleotide according to the present invention to the polymorphic marker allows PCR amplification of the segment pair. The amplified DNA segment can then be resolved by electrophoresis and autoradiography. A resulting autoradiography can then be analyzed for its similarity to another DNA segment autoradiography. Following the PCR amplification procedure, electrophoretic motility enhancing DNA analogs may optionally be used to increase the accuracy of the electrophoresis step.

Twenty-seven other primary pair sequences for detecting unique polymorphisms are sequences according to SEQ ID NO:10 through SEQ ID NO:63.

The described polymorphisms are useful for human sample individualization, because of their high PIC values. Since the described polymorphisms are based on the polymerase chain reaction, only minute amounts of genomic DNA are required for each test. The target sequences range from 69–260 bps in length so that high molecular weight DNA is not necessary and common problems such as shearing of DNA will have minimal impact on the performance of the assay. The assay is easy to perform and results can be obtained within 24 hours. Microsatellite repeat polymorphisms have been shown to be useful tools in DNA analysis. The 27 polymorphisms described here are original and are based on previously sequenced human genes. The most commonly used technique in forensic screening is based minisatellite markers in distinction to the PCR able microsatellites described here.

The 27 markers are characterized by sets of oligonucleotide primers as follows:

| Pair # | Locus | Chromosonal Location | Primer SEQ ID NO: | Heteroz | PIC | Size | Repeat | No. of alleles |
|---|---|---|---|---|---|---|---|---|
| 1A | Int-2 | 11q13 | 10,11 | 84.6% | 0.79 | 161–177 | (TG)$_5$TC(TG)$_{16}$ | 9 |
| 2A | PLA-AZ | 12 | 12,13 | 73.3% | 0.76 | 122–137 | (TTA)$_{16}$ | 6 |
| 3A | FABP2 | 4q28–q31 | 14,15 | 64% | 0.64 | 99–117 | (TTA)$_{13}$ | 6 |
| 4A | THROO1 | 15q15 | 16,17 | 60% | 0.58 | 165–181 | (CT)$_{14}$ | 9 |
| 5A | CYARP450 | 1SFq21.1 | 18,19 | 91.3% | 0.67 | 175–199 | (TTTA)$_8$ | 5 |
| 6A | GCG | 2q36–q37 | 20,21 | 88% | 0.77 | 142–172 | (GA)$_{19}$ | 11 |
| 7A | IL-9 | 5q | 22,23 | 62.5% | 0.75 | 127–139 | (TG)$_{20}$ | 7 |
| 8A | CSTP1 | 20 | 24,25 | 61% | 0.58 | 123–141 | (GT)$_{15}$ | |
| 9A | ANKYRIN | 8p11.1–21.1 | 26,27 | 54% | 0.45 | 107–113 | (AC)$_{14}$ | 4 |
| 10A | CD-19 | 16 | 28,29 | 40% | 0.39 | 79–91 | (GT)$_{17}$ | 7 |
| 11A | c-fms | 5q33.3–34 | 30,31 | 86% | 0.85 | 95–127 | (GT)$_{26}$ | 10 |
| 12A | CD 8 | 2p12 | 32,33 | 71% | 0.66 | 138–170 | (AC)$_{14}$ | 7 |
| 13A | CYP2D7-8 | 22 | 34,35 | 80% | 0.78 | 98–116 | (GT)$_{18}$ | 10 |
| 14A | W 30 | 7q | 36,37 | 74% | 0.72 | | | 11 |
| 15A | HMG-14 | 21 | 38,39 | 69% | 0.67 | 69–93 | (GT)$_{19}$ | 10 |
| 16A | RHO | 3 | 40,41 | 72% | 0.68 | 145–169 | | 5 |
| 17A | PPKL | 21q22.3 | 42,43 | 70% | 0.66 | 129–145 | (AC)$_{16}$ | 7 |
| 18A | HSFLT | 13q12 | 44,45 | 51% | 0.49 | 164–186 | (TG)$_{21}$ | 8 |
| 19A | HSMYHO1 | 14 | 46,47 | 66% | 0.60 | 90–102 | (GT)$_{15}$ | 6 |

-continued

| Pair # | Locus | Chromosonal Location | Primer SEQ ID NO: | Heteroz | PIC | Size | Repeat | No. of alleles |
|---|---|---|---|---|---|---|---|---|
| 20A | HSATPSY1 | 12p13-qter | 48,49 | 60% | 0.54 | 111–117 | $(GT)_{11}$ | 4 |
| 21A | CFES PPS | 15q25-qter | 50,51 | 75% | 0.70 | 143–163 | $(ATTT)_{11}$ | 6 |
| 22A | DHPRP2 | 6 | 52,53 | 70% | 0.66 | 157–173 | $(AAAC)_7$ | 5 |
| 23A | CRYG1 | 2q34–35 | 54,55 | 68% | 0.61 | 117–126 | $(AAC)_9$ | 4 |
| 24A | F13A1 | 6p24–25 | 56,57 | 78% | 0.75 | 180–230 | $(AAAG)_7$ | 8 |
| 25A | TRM1 | 6p23–q12 | 58,59 | 54% | 0.50 | 174–186 | $(AAC)_8$ | 5 |
| 26A | II-D | 6 | 60,61 | 81% | 0.78 | 185–206 | $(CAG)_{18}$ | |
| 27A | TH | 11p15.5-P15 | 62,63 | 78% | 0.75 | 244–260 | $(TCAT)_9$ | 5 |

Also, the invention relates to a method for conducting a PCR procedure comprising using an effective amount of at least one nucleotide according to according to the invention as set forth above, wherein the nucleotide is part of a primer pair of nucleotides selected from the group of nucleotide pairs consisting of a) a nucleotide sequence having the sequence as set forth in SEQ ID NO:1 and a nucleotide sequence as set forth in SEQ ID NO:2;

b) a nucleotide sequence having the sequence as set forth in SEQ ID NO:3 and a nucleotide sequence as set forth in SEQ ID NO:4;

c) a nucleotide sequence having the sequence as set forth in SEQ ID NO:5 and a nucleotide sequence as set forth in SEQ ID NO:6;

d) a nucleotide sequence having the sequence as set forth in SEQ ID NO:10 and a nucleotide sequence as set forth in SEQ ID NO:11;

e) a nucleotide sequence having the sequence as set forth in SEQ ID NO:12 and a nucleotide sequence as set forth in SEQ ID NO:13;

f) a nucleotide sequence having the sequence as set forth in SEQ ID NO:14 and a nucleotide sequence as set forth in SEQ ID NO:15;

g) a nucleotide sequence having the sequence as set forth in SEQ ID NO:16 and a nucleotide sequence as set forth in SEQ ID NO:17;

h) a nucleotide sequence having the sequence as set forth in SEQ ID NO:18 and a nucleotide sequence as set forth in SEQ ID NO:19;

i) a nucleotide sequence having the sequence as set forth in SEQ ID NO:20 and a nucleotide sequence as set forth in SEQ ID NO:21;

j) a nucleotide sequence having the sequence as set forth in SEQ ID NO:22 and a nucleotide sequence as set forth in SEQ ID NO:23;

k) a nucleotide sequence having the sequence as set forth in SEQ ID NO:24 and a nucleotide sequence as set forth in SEQ ID NO:25;

l) a nucleotide sequence having the sequence as set forth in SEQ ID NO:26 and a nucleotide sequence as set forth in SEQ ID NO:27;

m) a nucleotide sequence having the sequence as set forth in SEQ ID NO:28 and a nucleotide sequence as set forth in SEQ ID NO:29;

n) a nucleotide sequence having the sequence as set forth in SEQ ID NO:30 and a nucleotide sequence as set forth in SEQ ID NO:31;

o) a nucleotide sequence having the sequence as set forth in SEQ ID NO:32 and a nucleotide sequence as set forth in SEQ ID NO:33;

p) a nucleotide sequence having the sequence as set forth in SEQ ID NO:34 and a nucleotide sequence as set forth in SEQ ID NO:35;

q) a nucleotide sequence having the sequence as set forth in SEQ ID NO:36 and a nucleotide sequence as set forth in SEQ ID NO:37;

r) a nucleotide sequence having the sequence as set forth in SEQ ID NO:38 and a nucleotide sequence as set forth in SEQ ID NO:39;

s) a nucleotide sequence having the sequence as set forth in SEQ ID NO:40 and a nucleotide sequence as set forth in SEQ ID NO:41;

t) a nucleotide sequence having the sequence as set forth in SEQ ID NO:42 and a nucleotide sequence as set forth in SEQ ID NO:43;

u) a nucleotide sequence having the sequence as set forth in SEQ ID NO:44 and a nucleotide sequence as set forth in SEQ ID NO:45;

v) a nucleotide sequence having the sequence as set forth in SEQ ID NO:46 and a nucleotide sequence as set forth in SEQ ID NO:47;

w) a nucleotide sequence having the sequence as set forth in SEQ ID NO:48 and a nucleotide sequence as set forth in SEQ ID NO:49;

x) a nucleotide sequence having the sequence as set forth in SEQ ID NO:50 and a nucleotide sequence as set forth in SEQ ID NO:51;

y) a nucleotide sequence having the sequence as set forth in SEQ ID NO:52 and a nucleotide sequence as set forth in SEQ ID NO:53;

z) a nucleotide sequence having the sequence as set forth in SEQ ID NO:54 and a nucleotide sequence as set forth in SEQ ID NO:55;

aa) a nucleotide sequence having the sequence as set forth in SEQ ID NO:56 and a nucleotide sequence as set forth in SEQ ID NO:57;

bb) a nucleotide sequence having the sequence as set forth in SEQ ID NO:58 and a nucleotide sequence as set forth in SEQ ID NO:59;

cc) a nucleotide sequence having the sequence as set forth in SEQ ID NO:60 and a nucleotide sequence as set forth in SEQ ID NO:61;

dd) a nucleotide sequence having the sequence as set forth in SEQ ID NO:62 and a nucleotide sequence as set forth in SEQ ID NO:63.

Therefore, the invention further relates to an assay for measuring the subtle differences in genetic material regarding an added or omitted set of dinucleotide or tetranucleotide repeat polymorphisms selected from the group consisting of a sequence according to SEQ ID NO:7, a sequence according to SEQ ID NO:8 and a sequence according to SEQ ID NO:9, which comprises a. obtaining nucleotide segments comprising said repeat polymorphisms in an amount effective for testing, b. amplifying said segments by a PCR procedure using a pair of oligonucleotide primers capable of amplifying said polymorphism containing segments, c. resolving the amplified segments using page gels electrophoresis, and d. comparing the resolved segments by autoradiography to observe the differences in migration patterns due to length variation.

Preferably, the invention further relates to an assay for measuring the subtle differences in genetic material regarding an added or omitted set of dinucleotide or tetranucleotide repeat polymorphisms selected from the group consisting of a sequence according to SEQ ID NO:7, a sequence according to SEQ ID NO:8 and a sequence according to SEQ ID NO:9, which comprises a. obtaining nucleotide segments comprising said repeat polymorphisms in an amount effective for testing, b. amplifying said segments by a PCR procedure using the pair of oligonucleotide primers selected from the group consisting of a sequence according to SEQ ID NO:1, a sequence according to SEQ ID NO:2, a sequence according to SEQ ID NO:3, a sequence according to SEQ ID NO:4, a sequence according to SEQ ID NO:5, or a sequence according to SEQ ID NO:6, c. resolving the amplified segments using page gels electrophoresis, and d. comparing the resolved segments by autoradiography to observe the differences in migration patterns due to length variation.

Still further, the invention relates to an assay kit for conducting a PCR procedure comprising an effective amount of at least one nucleotide having a sequence according to the invention as set forth above, wherein the nucleotide is part of a primer pair of nucleotides selected from the group of nucleotide pairs consisting of a) a nucleotide sequence having the sequence as set forth in SEQ ID NO:1 and a nucleotide sequence as set forth in SEQ ID NO:2;

b) a nucleotide sequence having the sequence as set forth in SEQ ID NO:3 and a nucleotide sequence as set forth in SEQ ID NO:4; and c) a nucleotide sequence having the sequence as set forth in SEQ ID NO:5 and a nucleotide sequence as set forth in SEQ ID NO:6, d) a nucleotide sequence having the sequence as set forth in SEQ ID NO:10 and a nucleotide sequence as set forth in SEQ ID NO:11;

e) a nucleotide sequence having the sequence as set forth in SEQ ID NO:12 and a nucleotide sequence as set forth in SEQ ID NO:13;

f) a nucleotide sequence having the sequence as set forth in SEQ ID NO:14 and a nucleotide sequence as set forth in SEQ ID NO:15;

g) a nucleotide sequence having the sequence as set forth in SEQ ID NO:16 and a nucleotide sequence as set forth in SEQ ID NO:17;

h) a nucleotide sequence having the sequence as set forth in SEQ ID NO:18 and a nucleotide sequence as set forth in SEQ ID NO:19;

i) a nucleotide sequence having the sequence as set forth in SEQ ID NO:20 and a nucleotide sequence as set forth in SEQ ID NO:21;

j) a nucleotide sequence having the sequence as set forth in SEQ ID NO:22 and a nucleotide sequence as set forth in SEQ ID NO:23;

k) a nucleotide sequence having the sequence as set forth in SEQ ID NO:24 and a nucleotide sequence as set forth in SEQ ID NO:25;

l) a nucleotide sequence having the sequence as set forth in SEQ ID NO:26 and a nucleotide sequence as set forth in SEQ ID NO:27;

m) a nucleotide sequence having the sequence as set forth in SEQ ID NO:28 and a nucleotide sequence as set forth in SEQ ID NO:29;

n) a nucleotide sequence having the sequence as set forth in SEQ ID NO:30 and a nucleotide sequence as set forth in SEQ ID NO:31;

o) a nucleotide sequence having the sequence as set forth in SEQ ID NO:32 and a nucleotide sequence as set forth in SEQ ID NO:33;

p) a nucleotide sequence having the sequence as set forth in SEQ ID NO:34 and a nucleotide sequence as set forth in SEQ ID NO:35;

q) a nucleotide sequence having the sequence as set forth in SEQ ID NO:36 and a nucleotide sequence as set forth in SEQ ID NO:37;

r) a nucleotide sequence having the sequence as set forth in SEQ ID NO:38 and a nucleotide sequence as set forth in SEQ ID NO:39;

s) a nucleotide sequence having the sequence as set forth in SEQ ID NO:40 and a nucleotide sequence as set forth in SEQ ID NO:41;

t) a nucleotide sequence having the sequence as set forth in SEQ ID NO:42 and a nucleotide sequence as set forth in SEQ ID NO:43;

u) a nucleotide sequence having the sequence as set forth in SEQ ID NO:44 and a nucleotide sequence as set forth in SEQ ID NO:45;

v) a nucleotide sequence having the sequence as set forth in SEQ ID NO:46 and a nucleotide sequence as set forth in SEQ ID NO:47;

w) a nucleotide sequence having the sequence as set forth in SEQ ID NO:48 and a nucleotide sequence as set forth in SEQ ID NO:49;

x) a nucleotide sequence having the sequence as set forth in SEQ ID NO:50 and a nucleotide sequence as set forth in SEQ ID NO:51;

y) a nucleotide sequence having the sequence as set forth in SEQ ID NO:52 and a nucleotide sequence as set forth in SEQ ID NO:53;

z) a nucleotide sequence having the sequence as set forth in SEQ ID NO:54 and a nucleotide sequence as set forth in SEQ ID NO:55;

aa) a nucleotide sequence having the sequence as set forth in SEQ ID NO:56 and a nucleotide sequence as set forth in SEQ ID NO:57;

bb) a nucleotide sequence having the sequence as set forth in SEQ ID NO:58 and a nucleotide sequence as set forth in SEQ ID NO:59;

cc) a nucleotide sequence having the sequence as set forth in SEQ ID NO:60 and a nucleotide sequence as set forth in SEQ ID NO:61; and dd) a nucleotide sequence having the sequence as set forth in SEQ ID NO:62 and a nucleotide sequence as set forth in SEQ ID NO:63;

wherein said nucleotide is in combination with an effective amount of ancillary PCR reagents.

Accordingly, the above described polymorphisms are useful for human sample individualization, because of their high PIC values. Since the described polymorphic systems are based on the polymerase chain reaction (PCR), only minute (40 nanograms) amounts of genomic DNA are required for each test. The target sequences range from 92 to 310 base pairs so that high molecular weight DNA is not necessary, and common problems such as shearing of DNA will have minimal impact on the performance of the assay. The assay is easy to perform and results can be obtained within 24 hours. It is not uncommon for results to be available within 3-4 hours. By comparison, the prior art methods require a number of days before results are available, usually 3-4 days are required.

Also, the polymorphism corresponding to 1A-27A as described above and characterizes by their 27 primer pairs according to SEQ ID NO:10-SEQ NO:63 are useful for human sample individualization evaluation because of their high PIC values.

Further, the assay according to the invention is able to detect very small differences in nucleotide sequences. A single omission or addition of the repeat sequence will change the mobility due to the electrical nature and molecular weight of the target nucleotide sequence. These differences are clearly visible on the autoradiographs after electrophoresis.

Microsatellite repeat polymorphisms have been shown to be useful tools in DNA analysis. The three polymorphisms described here are original and are based on previously sequenced genes. The two tetranucleotide repeat markers described, can be scored easily since allele sizes differ by four base pairs. The most commonly used technique used in forensic screening is based on minisatellite markers, in distinction to the PCR able microsatellites described in the present invention.

The general PCR technique step is conducted generally as described in U.S. Pat. No. 4,683,195 to Mullis et al and U.S. Pat. No. 4,683,202 to Mullis et al, which are hereby incorporated by reference thereto. Further, electrical motility enhancing DNA analogs can optionally be used during the replication and amplification PCR procedure.

The degree of polymorphism in the genetic segments according to the present invention, which polymorphisms yield highly informative identification test results, is surprising and unexpected. The high PIC value (approximately 0.9) is totally unexpected.

Accordingly, the use of a PCR procedure and PCR primers pairs, such as those primer sequences according to SEQ ID NO:1 to SEQ ID NO:6, to detect the polymorphism DNA segment according to the present invention yields excellent results. Further use of primer sequences corresponding to SEQ ID NO:10 through SEQ ID NO:63 to detect the polymorphism yields excellent results. Such results are sufficiently accurate and informative to accurately identify DNA segments and determine degrees of relationship between DNA segments of individuals. Moreover, conducting three sets of PCR procedures on the same DNA segment samples while using a different PCR primer pair according to the present invention for each of the three procedures yields extraordinarily accurate and informative test results. Comparison of the three sets of test results data provides extremely accurate DNA segment identification.

The following examples are provided to more specifically describe the invention which is not limited to the following examples.

The described oligonucleotide primers are used to amplify the target sequences using PCR, under the following conditions:

EXAMPLE 1

The samples are of DNA are prepared as follows.

60 ng of genomic DNA are used as template for PCR with 80 ng of each oligonucleotide primer, 0.6 units of Taq Polymerase 50 mM KCL, 10 mM Tris (pH 8.3), 1.5 mM $MgCl_2$, 0.01% gelatin, 200 uM of each dGTP, dATP, dTTP, 2.5 uM dCTP and 10 microcuries of alpha P32 dCTP., in a final reaction volume of 15 microliters. The samples are overlaid with 15 microliters of mineral oil to prevent evaporation.

EXAMPLE 2

PCR is performed for each of the samples and primers described in Example 1, above.

PCR is performed in a Techne MW-1 microplate thermocycler under the following conditions denaturation of 94 degrees C. for 1.4 min., annealing at 55 degrees C. for 2 min., and extension at 72 degrees C. for 2 min. The cycle is repeated 30 times with a final extension at 72 degrees C for 10 min.

EXAMPLE 3

The amplified DNA segments from each of the samples described in Example 2 above are resolved by electrophoresis as follows.

Two microliters of each PCR reaction mixture sample are electrophoresed on a 6% PAGE sequencing gel and visualized by autoradiography. Exposure times for the autoradiography range from 3-16 hours.

The foregoing description of the specific embodiments will so fully reveal the general nature of the invention that others can, by applying current knowledge, readily modify and/or adapt for various applications such specific embodiments without departing from the generic concept and therefore such adaptations are intended to be comprehended within the meaning and range of equivalents of a disclosed embodiment. It is to be understood that the phraseology or terminology employed herein is for the purposes of description only and not of limitation.

---

We claim:

1. An oligonucleotide primer selected from the group consisting of a sequence according to SEQ ID NO:10 through SEQ ID NO: 35 and SEQ ID NO: 38 through SEQ ID NO:63.

2. A method for conducting a polymerase chain reaction procedure to detect an added or omitted set of dinucleotide or tetranucleotide repeat polymorphisms, comprising (A) obtaining a polynucleotide sample in an amount effective for testing;

(B) using an effective amount of at least one oligonucleotide primer according to claim 1, wherein the oligonucleotide primer is used as part of a pair of oligonucleotide primers selected from the group consisting of a) a sequence as set forth in SEQ ID NO:10 and a sequence as set forth in SEQ ID NO:11;

b) a sequence as set forth in SEQ ID NO:12 and a sequence as set forth in SEQ ID NO:13;

c) a sequence as set forth in SEQ ID NO:14 and a sequence as set forth in SEQ ID NO:15;

d) a sequence as set forth in SEQ ID NO:16 and a sequence as set forth in SEQ ID NO:17;

e) a sequence as set forth in SEQ ID NO:16 and a sequence as set forth in SEQ ID NO:19;

f) a sequence as set forth in SEQ ID NO:20 and a sequence as set forth in SEQ ID NO:21;

g) a sequence as set forth in SEQ ID NO:22 and a sequence as set forth in SEQ ID NO:23;

h) a sequence as set forth in SEQ ID NO:24 and a sequence as set forth in SEQ ID NO:25;

i) a sequence as set forth in SEQ ID NO:26 and a sequence as set forth in SEQ ID NO:27;

j) a sequence as set forth in SEQ ID NO:28 and a sequence as set forth in SEQ ID NO:29;

k) a sequence as set forth in SEQ ID NO:30 and a sequence as set forth in SEQ ID NO:31;

l) a sequence as set forth in SEQ ID NO:32 and a sequence as set forth in SEQ ID NO:33;

m) a sequence as set forth in SEQ ID NO:34 and a sequence as set forth in SEQ ID NO:35;

n) a sequence as set forth in SEQ ID NO:38 and a sequence as set forth in SEQ ID NO:39;

o) a sequence as set forth in SEQ ID NO:40 and a sequence as set forth in SEQ ID NO:41;
p) a sequence as set forth in SEQ ID NO:42 and a sequence as set forth in SEQ ID NO:43;
q) a sequence as set forth in SEQ ID NO:44 and a sequence as set forth in SEQ ID NO:45;
r) a sequence as set forth in SEQ ID NO:46 and a sequence as set forth in SEQ ID NO:47;
s) a sequence as set forth in SEQ ID NO:48 and a sequence as set forth in SEQ ID NO:49;
t) a sequence as set forth in SEQ ID NO:50 and a sequence as set forth in SEQ ID NO:51;
u) a sequence as set forth in SEQ ID NO:52 and a sequence as set forth in SEQ ID NO:53;
v) a sequence as set forth in SEQ ID NO:54 and a sequence as set forth in SEQ ID NO:55;
w) a sequence as set forth in SEQ ID NO:56 and a sequence as set forth in SEQ ID NO:57;
x) a sequence as set forth in SEQ ID NO:58 and a sequence as set forth in SEQ ID NO:59;
y) a sequence as set forth in SEQ ID NO:60 and a sequence as set forth in SEQ ID NO:61; and
z) a sequence as set forth in SEQ ID NO:62 and a sequence as set forth in SEQ ID NO:63; and (C) amplifying said sample by said polymerase chain reaction procedure using said pair of oligonucleotide primers capable of amplifying said sample and detecting said polymorphisms.

3. An assay for measuring the subtle differences in genetic material regarding an added or omitted set of dinucleotide or tetranucleotide repeat polymorphisms wherein said genetic material comprises a sequence characterized by a pair of oligonucleotide primers selected from the group consisting of sequence ID NOs: 10–35 and SEQ ID Nos 38–63, which comprises
  a. obtaining polynucleotide segments comprising said repeat polymorphisms in an amount effective for testing,
  b. amplifying said segments by a polymerase chain reaction procedure using a pair of oligonucleotide primers of claim 2 capable of amplifying said polymorphism containing segments,
  c. resolving the amplified segments using polyacrylamide gel electrophoresis, and
  d. comparing the resolved segments by autoradiography to observe the differences in migration patterns due to length variation.

4. An assay kit for conducting a polymerase chain reaction procedure comprising an effective amount of at least one oligonucleotide primer having a sequence according to claim 1, wherein the oligonucleotide is part of a pair of oligonucleotide primers selected from the group consisting of a) a sequence as set forth in SEQ ID NO:10 and a sequence as set forth in SEQ ID NO:11;
b) a sequence as set forth in SEQ ID NO:12 and a sequence as set forth in SEQ ID NO:13;
c) a sequence as set forth in SEQ ID NO:14 and a sequence as set forth in SEQ ID NO:15;
d) a sequence as set forth in SEQ ID NO:16 and a sequence as set forth in SEQ ID NO:17;
e) a sequence as set forth in SEQ ID NO:18 and a sequence as set forth in SEQ ID NO:19;
f) a sequence as set forth in SEQ ID NO:20 and a sequence as set forth in SEQ ID NO:21;
g) a sequence as set forth in SEQ ID NO:22 and a sequence as set forth in SEQ ID NO:23;
h) a sequence as set forth in SEQ ID NO:24 and a sequence as set forth in SEQ ID NO:25;
i) a sequence as set forth in SEQ ID NO:26 and a sequence as set forth in SEQ ID NO:27;
j) a sequence as set forth in SEQ ID NO:28 and a sequence as set forth in SEQ ID NO:29;
k) a sequence as set forth in SEQ ID NO:30 and a sequence as set forth in SEQ ID NO:31;
l) a sequence as set forth in SEQ ID NO:32 and a sequence as set forth in SEQ ID NO:33;
m) a sequence as set forth in SEQ ID NO:34 and a sequence as set forth in SEQ ID NO:35;
n) a sequence as set forth in SEQ ID NO:38 and a sequence as set forth in SEQ ID NO:39;
o) a sequence as set forth in SEQ ID NO:40 and a sequence as set forth in SEQ ID NO:41;
p) a sequence as set forth in SEQ ID NO:42 and a sequence as set forth in SEQ ID NO:43;
q) a sequence as set forth in SEQ ID NO:44 and a sequence as set forth in SEQ ID NO:45;
r) a sequence as set forth in SEQ ID NO:46 and a sequence as set forth in SEQ ID NO:47;
s) a sequence as set forth in SEQ ID NO:48 and a sequence as set forth in SEQ ID NO:49;
t) a sequence as set forth in SEQ ID NO:50 and a sequence as set forth in SEQ ID NO:51;
u) a sequence as set forth in SEQ ID NO:52 and a sequence as set forth in SEQ ID NO:53;
v) a sequence as set forth in SEQ ID NO:54 and a sequence as set forth in SEQ ID NO:55;
w) a sequence as set forth in SEQ ID NO:56 and a sequence as set forth in SEQ ID NO:57;
x) a sequence as set forth in SEQ ID NO:58 and a sequence as set forth in SEQ ID NO:59;
y) a sequence as set forth in SEQ ID NO:60 and a sequence as set forth in SEQ ID NO:61; and
z) a sequence as set forth in SEQ ID NO:62 and a sequence as set forth in SEQ ID NO:63;

wherein said effective amount of said oligonucleotide primer is in combination with an effective amount of ancillary polymerase chain reaction reagents.

* * * * *

SEQUENCE LISTING ( 1 ) GENERAL INFORMATION:

( i i i ) NUMBER OF SEQUENCES: 63

( 2 ) INFORMATION FOR SEQ ID NO:1:

( i ) SEQUENCE CHARACTERISTICS:
( A ) LENGTH: 20
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:1:

AATCTGGGCG ACAAGAGTGA    20

( 2 ) INFORMATION FOR SEQ ID NO:2:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

ACATCTCCCC TACCGCTATA    20

( 2 ) INFORMATION FOR SEQ ID NO:3:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

TCCAGCCTCG GAGACAGAAT    20

( 2 ) INFORMATION FOR SEQ ID NO:4:

( i ) SEQUENCE CHARACTERISTICS:
        ( A ) LENGTH: 21
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

AGTCCTTTCT CCAGAGCAGG T    21

( 2 ) INFORMATION FOR SEQ ID NO:5:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

GCCAGTGATG CTAAAGGTTG    20

( 2 ) INFORMATION FOR SEQ ID NO:6:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

AACATACGTG GCTCTATGCA    20

( 2 ) INFORMATION FOR SEQ ID NO:7:

( i ) SEQUENCE CHARACTERISTICS:
   ( A ) LENGTH: 291
   ( B ) TYPE: nucleic acid
   ( C ) STRANDEDNESS: single
   ( D ) TOPOLOGY: linear ( i i ) MOLECULE TYPE: DNA (genomic)

( x i ) SEQUENCE DESCRIPTION: SEQ ID NO:7:

```
AATCTGGGCG ACAAGAGTGA AACTCCGTCA AAAGAAAGAA AGAAAGAGAC AAAGAGAGTT    60
AGAAAGAAAG AAAGAGAGAG AGAGAGAAAG GAAGGAAGGA AGAAAAAGAA AGAAAAAGAA   120
AGAAAGAGAA AGAAAGAAAG AGAAAGAAAG AAAGAAAGAA AGAAAGAAAG AAAGAAAGAA   180
AGAAAGAAAA AGAAAGAAAG AAAGAAAGAA AGAAAGAAAG AAAGAAAGAA AGAAAGAAAG   240
AAAGAAAGGA AGGAAAGAAA GAGCAAGTTA CTATAGCGGT AGGGGAGATG T             291
```

( 2 ) INFORMATION FOR SEQ ID NO:8:

( i ) SEQUENCE CHARACTERISTICS:
      ( A ) LENGTH: 128
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:8:

```
GCCAGTGATG CTAAGGTTG TATTGCATAT ATACATATAT ATATATATAT ATATATATAT    60
ATATATATAT ATATATATAT ATATATATAT TTTAATTTGA TAGTATTGTG CATAGAGCCA   120
CGTATGTT                                                            128
```

( 2 ) INFORMATION FOR SEQ ID NO:9:

( i ) SEQUENCE CHARACTERISTICS:
      ( A ) LENGTH: 243
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:9:

```
TCCAGCCTCG GAGACAGAAT GAGACTCCAT CAAAAACAAG AAAGAAAGAA AGACAAAGAG    60
AGAAAGAAAG AAAGAAAGAA AGAAAGAAAG AGAGAGAGAG AGAGAGAGAG AGAAAGAAAG   120
AAAGAAAGAA AGAAAGAAAG AAAGAAAGAA AGAAAGAAAG AAAGAAAGAA GGAAAGAAAG   180
AAAGGAAACT AAAATAACTA AATAACTGAG TAGCACCACA CCACCTGCTC TGGAGAAAGG   240
ACT                                                                 243
```

( 2 ) INFORMATION FOR SEQ ID NO:10:

( i ) SEQUENCE CHARACTERISTICS:
      ( A ) LENGTH: 19
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:10:

```
TTTCTGGGTG TGTCTGAAT                                                 19
```

( 2 ) INFORMATION FOR SEQ ID NO:11:

( i ) SEQUENCE CHARACTERISTICS:
      ( A ) LENGTH: 20

( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

ACACAGTTGC TCTAAAGGGT        20

( 2 ) INFORMATION FOR SEQ ID NO:12:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

CTAGGTTGTA AGCTCCATGA        20

( 2 ) INFORMATION FOR SEQ ID NO:13:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

TTGAGCACTT ACTCTGTGCC        20

( 2 ) INFORMATION FOR SEQ ID NO:14:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

AACTCAGAAC AGTGCCTGAC        20

( 2 ) INFORMATION FOR SEQ ID NO:15:

( i ) SEQUENCE CHARACTERISTICS:
        ( A ) LENGTH: 21
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

ATTTCCCTCA AGGCTCCAGG T        21

( 2 ) INFORMATION FOR SEQ ID NO:16:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:16:

CTGATCTTGC TCACCTTCGA 20

(2) INFORMATION FOR SEQ ID NO:17:

(i) SEQUENCE CHARACTERISTICS:
        (A) LENGTH: 20
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

GCGTTTGCTG AAATGAAGGA 20

(2) INFORMATION FOR SEQ ID NO:18:

(i) SEQUENCE CHARACTERISTICS:
        (A) LENGTH: 20
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

GCAGGTACTT AGTTAGCTAC 20

(2) INFORMATION FOR SEQ ID NO:19:

(i) SEQUENCE CHARACTERISTICS:
        (A) LENGTH: 20
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

TTACAGTGAG CCAAGGTCGT 20

(2) INFORMATION FOR SEQ ID NO:20:

(i) SEQUENCE CHARACTERISTICS:
        (A) LENGTH: 20
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

TTTGTCTGGA TAGACTGGAG 20

(2) INFORMATION FOR SEQ ID NO:21:

(i) SEQUENCE CHARACTERISTICS:
        (A) LENGTH: 19
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:21:

CCATCTTCCT GTGGCTGTA 19

(2) INFORMATION FOR SEQ ID NO:22:

(i) SEQUENCE CHARACTERISTICS:

(A) LENGTH: 20
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:22:

CTAATGCAGA GATTTAGGGC                                                        20

(2) INFORMATION FOR SEQ ID NO:23:

(i) SEQUENCE CHARACTERISTICS:
            (A) LENGTH: 20
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:23:

GTGGTGTAAA GACTGCATAG                                                        20

(2) INFORMATION FOR SEQ ID NO:24:

(i) SEQUENCE CHARACTERISTICS:
            (A) LENGTH: 20
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:24:

ATGTGACTGA TGTGGGTCAG                                                        20

(2) INFORMATION FOR SEQ ID NO:25:

(i) SEQUENCE CHARACTERISTICS:
            (A) LENGTH: 20
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:25:

CATCTGCACT CATGCTCCAT                                                        20

(2) INFORMATION FOR SEQ ID NO:26:

(i) SEQUENCE CHARACTERISTICS:
            (A) LENGTH: 20
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:26:

TCCCAGATCG CTCTACATGA                                                        20

(2) INFORMATION FOR SEQ ID NO:27:

(i) SEQUENCE CHARACTERISTICS:
            (A) LENGTH: 20
            (B) TYPE: nucleic acid
            (C) STRANDEDNESS: single
            (D) TOPOLOGY: linear (ii) MOLECULE TYPE: DNA (genomic)

( x i ) SEQUENCE DESCRIPTION: SEQ ID NO:27:

CACAGCTTCA GAAGTCACAG                                                                                               20

( 2 ) INFORMATION FOR SEQ ID NO:28:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:28:

GAGCAATGTT GCTTAGGATG                                                                                               20

( 2 ) INFORMATION FOR SEQ ID NO:29:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:29:

TGGAAGTGTC ACTGGCATGT                                                                                               20

( 2 ) INFORMATION FOR SEQ ID NO:30:

( i ) SEQUENCE CHARACTERISTICS:
        ( A ) LENGTH: 21
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:30:

TGTGTCCAGC CTTAGTGTGC A                                                                                             21

( 2 ) INFORMATION FOR SEQ ID NO:31:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:31:

TCATCACTTC CAGAATGTGC                                                                                               20

( 2 ) INFORMATION FOR SEQ ID NO:32:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:32:

ACTGCCTCAT CCAGTTTCAG                                                                                               20

( 2 ) INFORMATION FOR SEQ ID NO:33:

(i) SEQUENCE CHARACTERISTICS:
    (A) LENGTH: 20
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:33:

GAGCAGGCAC TTGTTAGATG　　20

(2) INFORMATION FOR SEQ ID NO:34:

(i) SEQUENCE CHARACTERISTICS:
        (A) LENGTH: 20
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:34:

CCTCTTGGCT CTAACAGCAA　　20

(2) INFORMATION FOR SEQ ID NO:35:

(i) SEQUENCE CHARACTERISTICS:
        (A) LENGTH: 20
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:35:

AGCAAGACCC TGTCTCAAGA　　20

(2) INFORMATION FOR SEQ ID NO:36:

(i) SEQUENCE CHARACTERISTICS:
        (A) LENGTH: 20
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:36:

CAAGGCCCAT CTTCAGTAGA　　20

(2) INFORMATION FOR SEQ ID NO:37:

(i) SEQUENCE CHARACTERISTICS:
        (A) LENGTH: 20
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:37:

CCTTCTCACT CCTTTACTAG　　20

(2) INFORMATION FOR SEQ ID NO:38:

(i) SEQUENCE CHARACTERISTICS:
        (A) LENGTH: 20
        (B) TYPE: nucleic acid
        (C) STRANDEDNESS: single
        (D) TOPOLOGY: linear (ii) MOLECULE TYPE: DNA (genomic)

( x i ) SEQUENCE DESCRIPTION: SEQ ID NO:38:

GAAGACTGAG GAGGTCAGAA                                                                      20

( 2 ) INFORMATION FOR SEQ ID NO:39:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:39:

CTACTGTTCA GAGTCAAAGC                                                                      20

( 2 ) INFORMATION FOR SEQ ID NO:40:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:40:

TGCCCCACAT TAGGATGCAT                                                                      20

( 2 ) INFORMATION FOR SEQ ID NO:41:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:41:

AGGGACACGA ATCAGATCAG                                                                      20

( 2 ) INFORMATION FOR SEQ ID NO:42:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:42:

GTGGTACCTC ATTGTGGCTA                                                                      20

( 2 ) INFORMATION FOR SEQ ID NO:43:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:43:

AGGCATCCTT GTGCTGACAT                                                                      20

( 2 ) INFORMATION FOR SEQ ID NO:44:

( i ) SEQUENCE CHARACTERISTICS:
       ( A ) LENGTH: 20
       ( B ) TYPE: nucleic acid
       ( C ) STRANDEDNESS: single
       ( D ) TOPOLOGY: linear ( i i ) MOLECULE TYPE: DNA (genomic)

( x i ) SEQUENCE DESCRIPTION: SEQ ID NO:44:

TTTGGCCGAC AGTGGTGTAA                   20

( 2 ) INFORMATION FOR SEQ ID NO:45:

( i ) SEQUENCE CHARACTERISTICS:
           ( A ) LENGTH: 20
           ( B ) TYPE: nucleic acid
           ( C ) STRANDEDNESS: single
           ( D ) TOPOLOGY: linear ( i i ) MOLECULE TYPE: DNA (genomic)

( x i ) SEQUENCE DESCRIPTION: SEQ ID NO:45:

AGGACCAAAC CATGTCTGTC                   20

( 2 ) INFORMATION FOR SEQ ID NO:46:

( i ) SEQUENCE CHARACTERISTICS:
           ( A ) LENGTH: 20
           ( B ) TYPE: nucleic acid
           ( C ) STRANDEDNESS: single
           ( D ) TOPOLOGY: linear ( i i ) MOLECULE TYPE: DNA (genomic)

( x i ) SEQUENCE DESCRIPTION: SEQ ID NO:46:

CTGCATCTGA GCATATGGGA                   20

( 2 ) INFORMATION FOR SEQ ID NO:47:

( i ) SEQUENCE CHARACTERISTICS:
           ( A ) LENGTH: 20
           ( B ) TYPE: nucleic acid
           ( C ) STRANDEDNESS: single
           ( D ) TOPOLOGY: linear ( i i ) MOLECULE TYPE: DNA (genomic)

( x i ) SEQUENCE DESCRIPTION: SEQ ID NO:47:

CATTCAGACT ATGCAGGCTT                   20

( 2 ) INFORMATION FOR SEQ ID NO:48:

( i ) SEQUENCE CHARACTERISTICS:
           ( A ) LENGTH: 19
           ( B ) TYPE: nucleic acid
           ( C ) STRANDEDNESS: single
           ( D ) TOPOLOGY: linear ( i i ) MOLECULE TYPE: DNA (genomic)

( x i ) SEQUENCE DESCRIPTION: SEQ ID NO:48:

CTGGGACTAC TGGCACATG                    19

( 2 ) INFORMATION FOR SEQ ID NO:49:

( i ) SEQUENCE CHARACTERISTICS:
           ( A ) LENGTH: 19
           ( B ) TYPE: nucleic acid
           ( C ) STRANDEDNESS: single
           ( D ) TOPOLOGY: linear ( i i ) MOLECULE TYPE: DNA (genomic)

( x i ) SEQUENCE DESCRIPTION: SEQ ID NO:49:

GGCAACGTGG TGAAACCTT                                                                 19

( 2 ) INFORMATION FOR SEQ ID NO:50:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:50:

GGAAGATGGA GTGGCTGTTA                                                                20

( 2 ) INFORMATION FOR SEQ ID NO:51:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:51:

CTCCAGCCTG GCGAAAGAAT                                                                20

( 2 ) INFORMATION FOR SEQ ID NO:52:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:52:

GTAAGACTTT TGGAGCCATT                                                                20

( 2 ) INFORMATION FOR SEQ ID NO:53:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:53:

TTCAGGGAGA ATGAGATGGG                                                                20

( 2 ) INFORMATION FOR SEQ ID NO:54:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:54:

GACAGAGTGA GACTCCATCT                                                                20

( 2 ) INFORMATION FOR SEQ ID NO:55:

( i ) SEQUENCE CHARACTERISTICS:
    ( A ) LENGTH: 20
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:55:

GATCCTATCT TCTCAGGAGG                     20

( 2 ) INFORMATION FOR SEQ ID NO:56:

( i ) SEQUENCE CHARACTERISTICS:
    ( A ) LENGTH: 20
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:56:

GAGGTTGCAC TCCAGCCTTT                     20

( 2 ) INFORMATION FOR SEQ ID NO:57:

( i ) SEQUENCE CHARACTERISTICS:
    ( A ) LENGTH: 19
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:57:

ATGCCATGCA GATTAGAAA                      19

( 2 ) INFORMATION FOR SEQ ID NO:58:

( i ) SEQUENCE CHARACTERISTICS:
    ( A ) LENGTH: 19
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:58:

GGAAAGAAAC AGTGAAAGA                      19

( 2 ) INFORMATION FOR SEQ ID NO:59:

( i ) SEQUENCE CHARACTERISTICS:
    ( A ) LENGTH: 20
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:59:

ATCCATCGAC CTCTGGGTTA                     20

( 2 ) INFORMATION FOR SEQ ID NO:60:

( i ) SEQUENCE CHARACTERISTICS:
    ( A ) LENGTH: 20
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:60:

GACCCCACAG CCTATTCAGA 20

( 2 ) INFORMATION FOR SEQ ID NO:61:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:61:

TTGACTGCTG AACGGCTGCA 20

( 2 ) INFORMATION FOR SEQ ID NO:62:

( i ) SEQUENCE CHARACTERISTICS:
        ( A ) LENGTH: 19
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:62:

CAGCTGCCCT AGTCAGCAC 19

( 2 ) INFORMATION FOR SEQ ID NO:63:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:63:

GCTTCCGAGT GCAGGTCACA 20